(12) United States Patent
Kaplan

(10) Patent No.: US 9,440,909 B2
(45) Date of Patent: Sep. 13, 2016

(54) SULFIDE SCAVENGERS, METHODS FOR MAKING AND METHODS FOR USING

(71) Applicant: General Electric Company, Schenectady, NY (US)

(72) Inventor: Gregory Kaplan, Richboro, PA (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 14/755,269

(22) Filed: Jun. 30, 2015

(65) Prior Publication Data
US 2015/0299100 A1 Oct. 22, 2015

Related U.S. Application Data

(62) Division of application No. 13/404,214, filed on Feb. 24, 2012, now Pat. No. 9,108,899.

(60) Provisional application No. 61/581,710, filed on Dec. 30, 2011.

(51) Int. Cl.
| | |
|---|---|
| C07C 213/00 | (2006.01) |
| C02F 1/68 | (2006.01) |
| C10L 3/10 | (2006.01) |
| C10G 29/20 | (2006.01) |
| C07C 217/42 | (2006.01) |
| C07C 217/28 | (2006.01) |
| C10G 29/24 | (2006.01) |
| C02F 101/10 | (2006.01) |

(52) U.S. Cl.
CPC ............. *C07C 213/00* (2013.01); *C02F 1/68* (2013.01); *C07C 217/28* (2013.01); *C07C 217/42* (2013.01); *C10G 29/20* (2013.01); *C10G 29/24* (2013.01); *C10L 3/103* (2013.01); *C02F 2101/101* (2013.01); *C02F 2305/00* (2013.01); *C10G 2300/207* (2013.01); *C10L 2290/545* (2013.01)

(58) Field of Classification Search
None
See application file for complete search history.

(56) References Cited

U.S. PATENT DOCUMENTS

| | | | |
|---|---|---|---|
| 3,642,630 A | 2/1972 | MacPhail et al. | |
| 4,824,475 A | 4/1989 | Markley et al. | |
| 4,892,674 A | 1/1990 | Ho et al. | |
| 4,978,512 A | 12/1990 | Dillon | |
| 5,074,991 A | 12/1991 | Weers | |
| 5,190,640 A | 3/1993 | Roof et al. | |
| 5,347,004 A | 9/1994 | Rivers et al. | |
| 5,374,004 A | 12/1994 | von Behren | |
| 5,387,393 A | 2/1995 | Braden et al. | |
| 5,554,349 A | 9/1996 | Rivers et al. | |
| 5,674,377 A | 10/1997 | Sullivan, III et al. | |
| 6,242,598 B1 | 6/2001 | Stevenson et al. | |
| 6,710,213 B2 | 3/2004 | Aoki et al. | |
| 6,982,352 B2 | 1/2006 | Lappe et al. | |
| 7,115,215 B2 | 10/2006 | Titley et al. | |
| 7,140,433 B2 | 11/2006 | Gatlin et al. | |
| 7,268,134 B2 | 9/2007 | Timmer et al. | |
| 7,491,846 B2 | 2/2009 | Aoki et al. | |
| 7,517,447 B2* | 4/2009 | Gatlin | 208/236 |
| 2005/0153846 A1 | 7/2005 | Gatlin | |
| 2010/0197968 A1* | 8/2010 | Falana et al. | 564/502 |
| 2012/0012507 A1 | 1/2012 | Compton et al. | |
| 2013/0126429 A1* | 5/2013 | Lue | C10L 3/103 210/638 |

FOREIGN PATENT DOCUMENTS

| | | |
|---|---|---|
| CA | 2005946 | 6/1990 |
| CA | 2239587 | 12/1998 |
| EP | 0 8823 778 A2 | 12/1998 |

OTHER PUBLICATIONS

Zuivertz et al., "The Effect of Some Asymmetric Triazine Derivatives on the in Vitro Formation of Free Superoxide Radicals", Virologie, vol. 37, pp. 131-135, 1986.
Grant & Hackh's Chemical Dictionary, 5th Edition, p. 148, 1987.
Goodman et al., "Characterization by Electron Paramagnetic Resonance Spectroscopy of the Coordination Environment of Copper in Some Copper (II) Complexes of Asymmetric Triazines Having High Superoxide Dimutase Activity", Polyhedron, vol. 14, pp. 2523-2535, 1995.
Kickelbick et al., "Synthesis of Hexadentate Hexahydro-1, 3,5-Triazine-Based Ligands and their Copper (I) Complexes", Monatshefte fur Chemie / Chemical Monthy, vol. 133, pp. 1157-1164, 2002.
Guo et al., "A Convenient One-Pot Synthesis of Asymmetric 1, 3, 5-Triazine-2, 4, 6-Triones and Its Application Towards a Novel Class of Gonadotropin-Releasing Hormone Receptor Antagonists", Bioorganic & Medicinal Chemistry Letters, vol. 3, pp. 693-698, 2005.
International Search Report and Written Opinion mailed Jan. 17, 2013 for PCT/US2012/065666 filed Nov. 16, 2012.
International Preliminary Report on Patentability mailed Jul. 1, 2014 for PCT/US2012/065666 filed Nov. 16, 2012.

\* cited by examiner

*Primary Examiner* — Rebecca Anderson
*Assistant Examiner* — Po-Chih Chen
(74) *Attorney, Agent, or Firm* — Wegman, Hessler & Vanderburg

(57) ABSTRACT

Methods for making sulfide scavenging compositions are provided. The method comprises reacting at least one secondary amine with at least one aldehyde and solvent in the presence of a catalyst to form a reaction composition, wherein a reaction temperature is less than or equal to 90° C. Sulfide scavengers using the above method are also disclosed. Methods for removing sulfides from fluid streams are also provided. The methods include adding the above sulfide scavengers to fluid streams.

21 Claims, No Drawings

SULFIDE SCAVENGERS, METHODS FOR MAKING AND METHODS FOR USING

CROSS REFERENCE TO RELATED APPLICATIONS

This application is a divisional of U.S. patent application Ser. No. 13/404,214 filed Feb. 24, 2012 which, in turn, claimed priority of U.S. Provisional Application Ser. No. 61/581,710 filed Dec. 30, 2011; the contents of which are incorporated by reference herein.

FIELD OF THE INVENTION

This invention relates to methods and compositions for reacting with sulfides, and more particularly, for removing sulfides from fluid streams.

BACKGROUND OF THE INVENTION

The following description does not admit or imply that the method discussed below is citable as prior art or part of the general knowledge of a person skilled in the art in any particular country.

Hydrogen sulfide is a clear toxic gas with a foul odor. It is also highly flammable. The Environmental Protection Agency and other regulatory agencies worldwide strictly control the release of hydrogen sulfide into the environment. Hydrogen sulfide is often present in well water, waste water, and other aqueous streams. Hydrogen sulfide may also be present in crude oil and natural gas reserves and must be removed before using.

Generally, hydrocarbon streams can be treated with chemical scavengers to remove sulfides. These chemicals are called scavengers or sweetening agents. These chemical scavengers include adducts produced through the reaction of secondary amines and aldehydes. These secondary amine-aldehyde adduct scavengers include triazines, oxazolidines, Schiff bases, diamines, methyol adducts, and methylene bridge materials.

US2010/0197968 discloses aldehyde-amine sulfur scavenging compositions prepared by contacting an amine containing component and an aldehyde containing component in the presence of an alcohol.

US2005/0153846 discloses sulfur scavengers including monomeric aldehyde-amine adducts from the reaction of at least one sterically hindered primary or secondary amine and a molar excess of at least one aldehyde.

What is needed is an improved sulfide scavenger for removing sulfides from fluid streams.

SUMMARY OF THE INVENTION

It was surprisingly discovered that some secondary amine-aldehyde adducts contain byproducts, namely N-methyl secondary amines. These byproducts have a methyl group and lack an ether or polyether group, making them inert with respect to $H_2S$. These inert byproducts, or "inerts", are often present in scavengers made from amine-aldehyde adducts. The presence of inerts results in much higher storage and shipping costs due to sheer volume. Many of these inerts are also flammable. In addition, many inerts are soluble in hydrocarbon and thus can negatively affect downstream hydrocarbon applications. Negative effects include increasing the nitrogen content as well as increasing the likelihood of corrosion and fouling of processing equipment.

Inerts include cycloalkylmethylamines, dialkylmethylamines, and tertiary amines. Examples of inerts include, but are not limited to, diethylmethylamine, dipropylmethylamine (DPMA), dibutylmethylamine (DBMA), N-methyl piperazine, N-methyl piperidine, N-methyl morpholine, and N,N-dimethylmethanamine. It was also surprisingly discovered that the production of inerts can be controlled by controlling reaction conditions. The disclosed reaction conditions increase the yield of sulfide scavengers in secondary amine-aldehyde reactions while eliminating the need for a purification step.

In one embodiment, a method for making a sulfide scavenger is disclosed comprising reacting at least one secondary amine with at least one aldehyde and solvent in the presence of a catalyst to form a reaction composition, wherein the reaction temperature is less than or equal to about 90° C.

In another embodiment, the secondary amines used comprise at least one member selected from the group consisting of dimethylamine, diethylamine, dipropylamine, dipentylamine, diethanolamine, diglycolamine, diisopropanolamine, morpholine, piperazine, piperidine, diproylamine, dibutylamine, diisobutylamine, di-tertbutylamine, dipentylamine, diisopentylamine, dineopentylamine, dihexylamine, diheptylamine, dioctylamine, dinonylamine, didecylamine, diadamanylamine, butyl-propylamine, butyl-hexylamine, butyl-heptylamine, hexyl-heptylamine, butyl-heptylamine, hexyl-heptylamine, aniline, naphthyl amine, diphenylamine, dinaphthylamine, bis(monomethylphenyl)amine, bis(dimethylphenyl)amine, bis(trimethylphenyl)amine, dicyclopentylamine, dicyclohexylamine, dicyclooctylamine, N-cyclopentyl, N-cyclohexylamine, tetramethylamino bispropylamine, bis(4-aminocyclohexyl)methane, bis(4-aminophenyl)methane, 1,8-diazabicyclo[5.4.0]undec-7-ene, and bispicoylamine. In another embodiment, the secondary amines comprise di-n-propylamine. Alternatively, the secondary amines comprise di-n-butylamine.

In another embodiment, the aldehydes used comprise at least one member selected from the group consisting of formaldehyde, alkylaldehydes, arylaldehydes, methoxyaldehydes, hydroxyaldehydes, cinnaminaldehyde, glyceraldehydes, vanillin, veratraldehyde, alloxan, noneal, 1-formyl piperdine, salicylaldehyde, citronella, paraformaldehyde, methyl formal, acetaldehyde, paraldehyde, glycoladehyde, hydroxymethyl glyceraldehyde, butyl formal, trioxane, tetroxane, glyoxal, and methyl formcel.

In another embodiment, the catalyst comprises a base. In another embodiment, the base comprises an alkali hydroxide. In yet another embodiment, the alkali hydroxide comprises at least one member selected from the group consisting of sodium hydroxide and potassium hydroxide. The solvent may comprise at least one member selected from the group consisting of water and hydrocarbons. The molar ratio of aldehydes to secondary amines may range from about 1.1:1.0 to about 3.0:1.0. In another embodiment, the reaction temperature may be less than or equal to 70° C. Alternatively, the reaction temperature may be less than or equal to 60° C.

The weight percent (wt %) of the catalyst may range from about 1 wt % to about 5 wt % of the total weight of the reaction composition. In yet another embodiment, the wt % of the solvent may range from about 5 wt % to about 10 wt % of a total weight of the reaction composition.

Another embodiment discloses a sulfide scavenger prepared by any of the above embodiments. In another embodiment, the sulfide scavenger comprises less than about 5 wt % inerts therein. In yet another embodiment, the inerts comprise at least one member selected from the group consisting of diethylmethylamine, dipropylmethylamine (DPMA), dibutylmethylamine (DBMA), N-methyl piperazine, N-methyl piperidine, N-methyl morpholine, and N,N-dimethylmethanamine.

Another embodiment discloses a method for reducing sulfides from a fluid stream, wherein the sulfide scavenger was prepared by reacting at least one secondary amine with at least one aldehyde and solvent in the presence of a catalyst to form a reaction composition, and where the reaction temperature is less than or equal to about 90° C.

The method may be used to remove sulfides, including organic sulfides, mercaptans, thiols, COS, and $H_2S$. The fluid streams may include hydrocarbon and aqueous streams.

In another embodiment the sulfide scavengers used were prepared using a catalyst comprising at least one base. In another embodiment, the solvent used comprises at least one member selected from the group consisting of water and hydrocarbons. In yet another embodiment, the molar ratio of aldehyde to secondary amine ranges from about 1.1:1.0 to about 3.0:1.0.

In another embodiment, the sulfide scavengers were prepared at a reaction temperature less than or equal to about 70° C. Alternatively, the reaction temperature may be less than or equal to about 60° C.

In another embodiment, the sulfide scavengers used were prepared wherein the weight percent (wt %) of the catalyst ranged from about 1 wt % to about 5 wt % of the total weight the reaction composition. In yet another embodiment, the weight percent of the solvent ranges from about 5 wt % to about 10 wt % of the total weight of the reaction composition.

In another embodiment, the sulfide scavenger is added to the fluid stream in an amount ranging from about 10 to about 100,000 ppm by volume of the fluid stream. In another embodiment, the sulfide scavenger is added to the fluid stream in an amount ranging from about 100 to about 50,000 ppm by volume of the fluid stream. Alternatively, the sulfide scavenger is added to the fluid stream in an amount ranging from about 600 to about 3,000 ppm by volume of the fluid stream.

The various embodiments provide for an improved sulfide scavenger with reduced inerts therein. This sulfide scavenger has increased scavenging activity, reduced reaction times, reduced volume for easier storage and shipping, and increased safety for handling and storing the scavenger.

DETAILED DESCRIPTION OF THE INVENTION

The singular forms "a," "an" and "the" include plural referents unless the context clearly dictates otherwise. The endpoints of all ranges reciting the same characteristic are independently combinable and inclusive of the recited endpoint. All references are incorporated herein by reference.

The modifier "about" used in connection with a quantity is inclusive of the stated value and has the meaning dictated by the context (e.g., includes the tolerance ranges associated with measurement of the particular quantity).

"Optional" or "optionally" means that the subsequently described event or circumstance may or may not occur, or that the subsequently identified material may or may not be present, and that the description includes instances where the event or circumstance occurs or where the material is present, and instances where the event or circumstance does not occur or the material is not present.

The terms "comprises", "comprising", "includes", "including", "has", "having", "containing", "contains" or any other variation thereof, are intended to cover a non-exclusive inclusion. For example, a process, method, article or apparatus that comprises a list of elements is not necessarily limited to only those elements, but may include other elements not expressly listed or inherent to such process, method, article or apparatus.

This disclosure pertains to sulfide scavengers, methods of making and methods of use. Sulfide scavengers include adducts produced through the reaction of secondary amines and aldehydes. These secondary amine-aldehyde adduct scavengers include triazines, oxazolidines, Schiff bases, diamines, methyol adducts, and methylene bridge materials.

Suitable aldehydes include, without limitation, aldehydes having the formula R—CHO, such as formaldehyde, alkylaldehydes, arylaldehydes, methoxyaldehydes, hydroxyaldehydes, cinnaminaldehyde, glyceraldehydes, vanillin, veratraldehyde, alloxan, noneal, 1-formyl piperdine, salicylaldehyde, citronella, paraformaldehyde, methyl formal, acetaldehyde, paraldehyde, glycoladehyde, hydroxymethyl glyceraldehyde, butyl formal, trioxane, tetroxane, glyoxal, methyl formcel and mixtures thereof.

Suitable secondary amines include, but are not limited to, dialkylamines, dimethylamine, diethylamine, dipropylamine, dipentylamine, secondary alkanolamines, such as diethanolamine, diglycolamine, diisopropanolamine, morpholine, piperazine, piperidine, diproylamine, dibutylamine, diisobutylamine, di-tertbutylamine, dipentylamine, diisopentylamine, dineopentylamine, dihexylamine, diheptylamine, dioctylamine, dinonylamine, didecylamine, diadamanylamine, butyl-propylamine, butyl-hexylamine, butyl-heptylamine, hexyl-heptylamine, butyl-heptylamine, hexyl-heptylamine, aniline, naphthyl amine, diphenylamine, dinaphthylamine, bis(monomethylphenyl)amine, bis(dimethylphenyl)amine, bis(trimethylphenyl)amine, dicyclopentylamine, dicyclohexylamine, dicyclooctylamine, N-cyclopentyl, N-cyclohexylamine, tetramethylamino bispropylamine, bis(4-aminocyclohexyl)methane, bis(4-aminophenyl)methane, 1,8-diazabicyclo[5.4.0]undec-7-ene, bispicoylamine and mixtures thereof.

These secondary amines have the structure as set forth in Formula I or II:

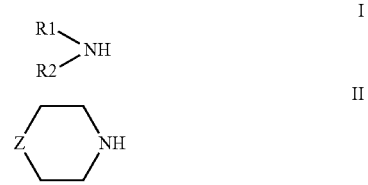

where $R_1$, and $R_2$ may be the same or different alkyls, hydroxyl-substituted alkyls, and alkoxy-substituted alkyls of 1 to 20 carbon atoms; the alkyl groups may be straight or branched alkyl groups, including, but not limited to, methyl, ethyl, propyl, butyl, hydroxylethyl, and methoxypropyl; and the cycloalkyl ring has an atom, Z, selected from the group consisting of carbon, oxygen, nitrogen, including NH (piperazine), piperidine, morpholine, and sulfur.

When reacted with formaldehyde, the above secondary amines form sulfide scavengers having the structure as set forth in Formula III, IV, or V:

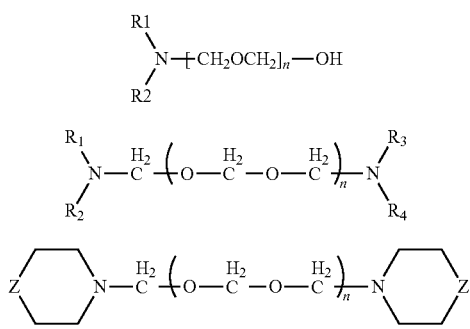

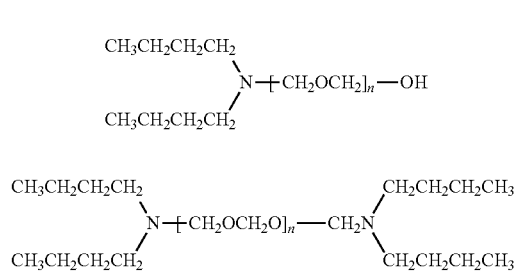

where n may be 1 to 100; where $R_1$, $R_2$, $R_3$, and $R_4$ may be the same or different alkyls, hydroxyl-substituted alkyls, and alkoxy-substituted alkyls of 1 to 20 carbon atoms; the alkyl groups may be straight or branched alkyl groups, including, but not limited to, methyl, ethyl, propyl, butyl, hydroxylethyl, and methoxypropyl; and the cycloalkyl ring has an atom, Z, selected from the group consisting of carbon, oxygen, nitrogen, including NH (piperazine), piperidine, morpholine, and sulfur. Alternative ranges for n include 1 to 20; 1 to 10; or 1 to 4.

When di-n-butylamine is used for the secondary amine, the resulting sulfide scavengers may have the structure as set forth in VI or VII:

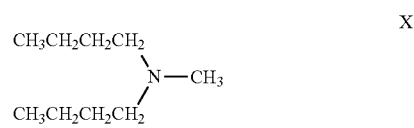

where n may be 1 to 100. Alternative ranges for n include 1 to 20; 1 to 10; or 1 to 4.

It was surprisingly discovered that some secondary amine-aldehyde adducts contain byproducts, namely N-methyl secondary amines. These byproducts have a methyl group and lack an ether or polyether group, making them inert with respect to H$_2$S. These inert byproducts, or "inerts", are often present in scavengers made from amine-aldehyde adducts. The presence of inerts results in much higher storage and shipping costs due to sheer volume. Many of these inerts are also flammable. In addition, many inerts are soluble in hydrocarbon and thus can negatively affect downstream hydrocarbon applications. Negative effects include increasing the nitrogen content as well as increasing the likelihood of corrosion and fouling of processing equipment.

Inerts include cycloalkylmethylamines, dialkylmethylamines, and tertiary amines and may have the structure as set forth in Formula VIII or IX:

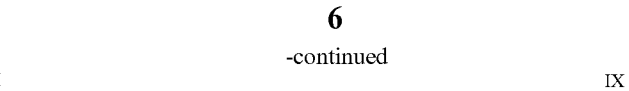

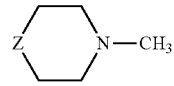

where $R_1$, and $R_2$ may be the same or different alkyls, hydroxyl-substituted alkyls, and alkoxy-substituted alkyls of 1 to 20 carbon atoms; the alkyl groups may be straight or branched alkyl groups, including, but not limited to, methyl, ethyl, propyl, butyl, hydroxylethyl, and methoxypropyl; and the cycloalkyl ring has an atom, Z, selected from the group consisting of carbon, oxygen, nitrogen, including NH (piperazine), piperidine, morpholine, and sulfur.

Examples of inerts include, but are not limited to, diethylmethylamine, dipropylmethylamine, dibutylmethylamine, N-methyl piperazine, N-methyl piperidine, N-methyl morpholine, and N,N-dimethylmethanamine.

One inert, dibutylmethylamine (DBMA) is also known as methyl-dibutylamine, N-methyl-di-n-butylamine, or N-butyl-N-methylbutan-1-amine. As with other types of deleterious N-methyl secondary amines, DBMA has a methyl group and lacks an ether or polyether group, making it inert with respect to hydrogen sulfide. DBMA has the structure and Formula X:

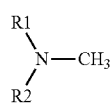

Inventors discovered the presence of DBMA (dibutylmethylamine) as a byproduct in the mixture produced by reaction of di-n-butylamine (DBA) and formaldehyde. The concentration of DBMA in such mixtures can reach levels up to 40%.

Since DBMA is completely inert in hydrogen sulfide scavenging application, its presence results in much higher storage and shipping costs due to sheer volume. DBMA is not only inert with respect to H$_2$S; it is flammable. In addition, DBMA is soluble in hydrocarbon and thus can negatively affect downstream hydrocarbon applications. Negative effects include increasing the nitrogen content as well as increasing the likelihood of corrosion and fouling of processing equipment.

Another inert, dipropylmethylamine (DPMA), is found in the mixture produced by the reaction of di-n-propylamine (DPA) and formaldehyde. It has negative effects similar to DBMA. DPA has a lower molecular weight and produces more active sulfide scavengers than DBA. Prior to the present invention, however, DBA was a preferred raw material for making sulfide scavengers. This was because DPMA production is even more temperature sensitive than DBMA, thus the concentration of DPMA in sulfide scavengers typically exceeded 60%.

It was surprisingly discovered, however, that the production of inerts, such as DBMA and DPMA can be controlled by controlling reaction conditions. The disclosed reaction conditions increase the yield of sulfide scavengers in secondary amine-aldehyde reactions while eliminating the need for a purification step.

It was discovered that the production of inerts increases with increased reaction temperature. Thus it is preferred to react secondary amines and aldehydes at reaction temperatures as low as possible. Prior to the present invention, the reaction temperature was limited to the temperature required to initiate the reaction. It was surprisingly discovered that adding a base as a catalyst to further increase the pH of an already caustic reaction mixture, lowered the initiation temperature for a secondary amine-aldehyde reaction. It was also surprisingly discovered that sulfide scavenging applications using sulfide scavengers made with DPA required less scavengers than applications where DBA-made scavengers were used. Because of the present invention, a more efficient scavenger may be made using DPA, further reducing cost.

In one embodiment, a method for making a sulfide scavenger is disclosed comprising reacting at least one secondary amine with at least one aldehyde and solvent in the presence of a catalyst to form a reaction composition, wherein the reaction temperature is less than or equal to about 90° C.

Suitable secondary amines include, but are not limited to, dialkylamines, dimethylamine, diethylamine, dipropylamine, dipentylamine, secondary alkanolamines, such as diethanolamine, diglycolamine, diisopropanolamine, morpholine, piperazine, piperidine, diproylamine, dibutylamine, diisobutylamine, di-tertbutylamine, dipentylamine, diisopentylamine, dineopentylamine, dihexylamine, diheptylamine, dioctylamine, dinonylamine, didecylamine, diadamanylamine, butyl-propylamine, butyl-hexylamine, butyl-heptylamine, hexyl-heptylamine, butyl-heptylamine, hexyl-heptylamine, aniline, naphthyl amine, diphenylamine, dinaphthylamine, bis(monomethylphenyl)amine, bis(dimethylphenyl)amine, bis(trimethylphenyl)amine, dicyclopentylamine, dicyclohexylamine, dicyclooctylamine, N-cyclopentyl, N-cyclohexylamine, tetramethylamino bispropylamine, bis(4-aminocyclohexyl)methane, bis(4-aminophenyl)methane, 1,8-diazabicyclo[5.4.0]undec-7-ene, bispicoylamine and mixtures thereof. In another embodiment, the secondary amines comprise di-n-propylamine. Alternatively, the secondary amines comprise di-n-butylamine.

In one embodiment, the secondary amine is present from about 40 percent by weight to about 80 percent by weight, based on the total weight of the reaction composition. In another embodiment, the secondary amine is present from about 50 percent by weight to about 70 percent by weight. In another embodiment, the secondary amine is present from about 55 percent by weight to about 65 percent by weight. In one embodiment, the secondary amine is present from about 60 percent by weight to about 65 percent by weight, based on the total weight of the reaction composition.

Suitable aldehydes include, without limitation, aldehydes having the formula R—CHO, such as formaldehyde, alkylaldehydes, arylaldehydes, methoxyaldehydes, hydroxyaldehydes, cinnaminaldehyde, glyceraldehydes, vanillin, veratraldehyde, alloxan, noneal, 1-formyl piperdine, salicylaldehyde, citronella, paraformaldehyde, methyl formal, acetaldehyde, paraldehyde, glycoladehyde, hydroxymethyl glyceraldehyde, butyl formal, trioxane, tetroxane, glyoxal, methyl formcel and mixtures thereof. In one embodiment, the aldehyde may be formaldehyde or a paraformaldehyde.

In another embodiment, the aldehyde is present from about 10 percent by weight to about 50 percent by weight, based on the total weight of the reaction composition. In another embodiment, the aldehyde is present from about 20 percent by weight to about 40 percent by weight. In another embodiment, the aldehyde is present from about 25 percent by weight to about 35 percent by weight. In one embodiment, the aldehyde is present from about 25 percent by weight to about 30 percent by weight, based on the total weight of the reaction composition.

The molar ratio of total aldehydes to amines may be from about 3.0:1 to about 1:3.0. Alternatively, the molar ratio of aldehydes to secondary amines may range from about 1.1:1.0 to about 3.0:1.0.

In another embodiment, the reaction temperature may be less than or equal to 80° C. In yet another embodiment, the reaction temperature may be less than or equal to 70° C. Alternatively, the reaction temperature may be less than or equal to 60° C. In yet another embodiment, the reaction proceeds at room temperature.

In one embodiment, a catalyst may be added to the reaction. In one embodiment, the catalyst comprises a base. In another embodiment, the catalyst comprises an alkali hydroxide. Suitable alkali hydroxides include, but are not limited to, potassium hydroxide, barium hydroxide, cesium hydroxide, sodium hydroxide, strontium hydroxide, calcium hydroxide, magnesium hydroxide, lithium hydroxide, and rubidium hydroxide. In another embodiment, the catalyst comprises at least one member selected from the group consisting of potassium hydroxide and sodium hydroxide. In one embodiment, the catalyst may be present from about 0.1 percent by weight to about 20 percent by weight, based on the total weight of the reaction composition. In another embodiment, the catalyst may be present from about 0.5 percent by weight to about 10 percent by weight. In yet another embodiment, the catalyst may be present from about 1 percent by weight to about 5 percent by weight, based on the total weight of the reaction composition.

The reaction may occur in solution. In one embodiment, the reaction includes a solvent. The sulfide scavengers produced are immiscible in water; therefore, suitable solvents include water and water-immiscible solvents. By using water or water-immiscible solvents, the sulfide scavengers produced may be easily separated from water. Specific examples of suitable solvents include, but are not limited to, water, benzene, or butanol. In another embodiment, the solvent may be a hydrocarbon or aqueous solvent. Suitable hydrocarbon solvents include, but are not limited to, aromatic and aliphatic hydrocarbons. Suitable aqueous solvents include water. In one embodiment, the solvent may comprise at least one member selected from the group consisting of water and hydrocarbons. There is no limit on how much solvent may be used. In another embodiment, the solvent may be present from about 1 percent by weight to about 30 percent by weight, based on the total weight of the reaction composition. In another embodiment, the solvent may be present from about 1 percent by weight to about 20 percent by weight. In another embodiment, the solvent may be present from about 5 percent by weight to about 15 percent by weight. In yet another embodiment, the solvent may be present from about 5 percent by weight to about 10 percent by weight, based on the total weight of the reaction composition.

Another embodiment discloses a sulfide scavenger prepared by any of the above methods. In another embodiment, the sulfide scavenger comprises less than about 60 percent by weight inerts therein. In another embodiment, the sulfide scavenger comprises less than about 30 wt % inerts therein. In yet another embodiment, the sulfide scavenger comprises less than about 5 percent by weight inerts therein. In another embodiment, the inerts comprise at least one member selected from the group consisting of diethylmethylamine, dipropylmethylamine (DPMA), dibutylmethylamine (DBMA), N-methyl piperazine, N-methyl piperidine, N-methyl morpholine, and N,N-dimethylmethanamine. The sulfide scavengers are more active, less flammable and introduce less nitrogen per scavenged sulfide. Savings come from higher yield, less waste, and lower storage and shipping costs.

Another embodiment discloses a method for reducing sulfides from a fluid stream, wherein the sulfide scavenger was prepared by reacting at least one secondary amine with at least one aldehyde and solvent in the presence of a catalyst to form a reaction composition, and where the temperature is less than or equal to about 90° C.

The method may be used to reduce sulfides, including organic sulfides, mercaptans, thiols, carbonyl sulfide (COS), and hydrogen sulfide ($H_2S$). A fluid stream encompasses both gaseous and liquid streams. In one embodiment, the fluid stream may be a fluid hydrocarbon stream or an aqueous fluid stream. Hydrocarbon streams may include unrefined and refined hydrocarbon products, natural gas, derivatives from petroleum or the liquefaction of coal, wellhead condensate, crude oil or distillates such as gasolines, distillate fuels, oils and residual fuels.

The fluid streams may be treated continuously or in a batch process near the wellhead. Continuous treatment installations near the wellhead may be used to inject scavengers directly into the hydrocarbon pipeline. The injection system may include a chemical injection pump and piping tees or atomization nozzles to introduce the scavengers into the pipeline. A length of the pipeline allows for contact between the scavenger and the sulfide. The scavengers may be used neat or diluted with hydrocarbons or alcohols.

In another embodiment the sulfide scavengers used were prepared using a catalyst comprising a base. In another embodiment, the solvent used comprises at least one member selected from the group consisting of water and hydrocarbons. In yet another embodiment, the molar ratio of aldehyde to secondary amine ranges from about 1.1:1.0 to about 3.0:1.0.

In another embodiment, the sulfide scavengers were prepared at a reaction temperature less than or equal to about 70° C. Alternatively, the reaction temperature may be less than or equal to about 60° C.

In another embodiment, the sulfide scavengers used were prepared wherein the weight percent (wt %) of the catalyst ranged from about 1 wt % to about 5 wt % of the total weight the reaction composition. In yet another embodiment, the weight percent of the solvent ranges from about 5 wt % to about 10 wt % of the total weight of the reaction composition.

The amount of sulfide scavengers added will depend on the application and amount of sulfide scavenging required. In natural gas reserves, for example, hydrogen sulfide may vary from less than 100 ppm to 3000 ppm. In one embodiment, the sulfide scavenger is added to the fluid stream in an amount ranging from about 10 to about 100,000 ppm by volume of the fluid stream. In another embodiment, the sulfide scavenger is added to the fluid stream in an amount ranging from about 100 to about 50,000 ppm by volume of the fluid stream. Alternatively, the sulfide scavenger is added to the fluid stream in an amount ranging from about 600 to about 3,000 ppm by volume of the fluid stream.

The various embodiments provide for an improved sulfide scavenger with increased scavenging activity, reduced reaction times, reduced volume for easier storage and shipping and increased safety for handling and storing the scavenger.

In order that those skilled in the art will be better able to practice the present disclosure, the following examples are given by way of illustration and not by way of limitation.

EXAMPLES

Example 1

31 g paraformaldehyde, 71 g of dibutylamine, 9 g of water and 2 g of a 25% by weight solution of sodium hydroxide were placed in a flask equipped with a stirrer and temperature control device. The reactants were heated to 80° C. and stirred for 2 hours at this temperature. After two hours, the mixing was stopped. The top organic layer was separated and washed with water and yielded 89 g of a clear, colorless liquid product of a secondary amine-aldehyde product. The product was analyzed by GC, showing the presence of 6.8% by weight of DMBA.

Comparative Example 1

A flask equipped with a stirrer, condenser, and temperature control device was charged with 1 Mole (31.25 gm) of 96% pure paraformaldehyde and 0.5 Mole (65.0 gm) of di-n-butylamine. Contents of the flask were stirred for 2 hours at 80° C. and for 2 hours at 90° C. The top organic layer was separated yielding 75 gm (87% yield) of a clear, colorless liquid as secondary amine-formaldehyde adducts (Product I). Product I was analyzed by GC, showing the presence of 41 wt % of dibutylmethylamine (DBMA) therein.

Comparative Example 2

In this example, 200 ml of a light hydrocarbon mixture having 2,000 ppm of $H_2S$ level in the head space was placed in a 1-liter bottle. Next, Product I produced in Comparative Example 1 was added to the 1-liter bottle at 3,800 ppm by volume of the hydrocarbon mixture. After stirring for 30 minutes at room temperature, the $H_2S$ level in the head space was reduced to <0.5 ppm.

Comparative Example 3

In this example, 200 ml of a light hydrocarbon mixture having 2,000 ppm of $H_2S$ level in the head space was placed in a 1-liter bottle. Next, dibutylmethylamine (DBMA) commercially available from Aldrich was added to the 1-liter bottle at 10,000 ppm by volume of the hydrocarbon mixture. After stirring for 30 minutes at room temperature, the $H_2S$ level in the head space remained at 2,000 ppm.

Example 2

A flask equipped with a stirrer, condenser, and temperature control device was charged with 1 Mole (31.25 gm) of 96% pure paraformaldehyde, 0.5 Mole (65.0 gm) of di-n-butylamine, and of 1.7 gm of 50% NaOH solution in water. Contents of the flask were stirred for 2 hours at 70° C. The top organic layer was separated yielding 86 gm (99%) of a clear, colorless liquid as secondary amine-formaldehyde adducts (Product II). Product II was analyzed by GC, showing the presence of 1.5 wt % of dibutylmethylamine (DBMA) therein.

Example 3

(DPA)

A flask equipped with a stirrer, condenser, and temperature control device was charged with 1 Mole (31.25 gm) of 96% pure paraformaldehyde, 0.58 Mole (58.0 gm) of di-n-propylamine, and 2 gm of 50% KOH solution in water. Contents of the flask were stirred for 2.5 hours at 60° C. The top organic layer was separated yielding 77 gm (99%) of a clear, colorless liquid as secondary amine-formaldehyde adducts (Product III). Product III was analyzed by GC, showing presence of 2.5 wt % of dipropylmethylamine (DPMA) therein.

Example 4

(DPA)

Reaction conditions similar to Example 3 were used, except the flask contents were stirred for 2 hours at 70° C. Analysis on the top organic layer showed the presence of 27% DPMA in the final product.

Example 5

(DPA)

Reaction conditions similar to Example 3 were used, except the flask contents were stirred for 2 hours at 80° C. Analysis on the top organic layer showed the presence of 53% DPMA in the final product.

Example 6

In this example, 200 ml of a light hydrocarbon mixture having 2,000 ppm of $H_2S$ level in the head space was placed in a 1-liter bottle. Next, Product II produced in Example 2 was added to the 1-liter bottle at 2,150 ppm by volume of the hydrocarbon mixture. After stirring for 30 minutes at room temperature, the $H_2S$ level in the head space was reduced to <0.5 ppm.

Turning to Comparative Example 2, where 3,800 ppm by volume of sulfide scavenger was required, Example 6 demonstrates a 43% improvement in $H_2S$ scavenging efficiency compared to Product I produced in Comparative Example 2. The improvement resulted from decreasing the yield of DBMA.

Example 7

(DPA)

In this example, 200 ml of a light hydrocarbon mixture having 2,000 ppm of $H_2S$ level in the head space was placed in a 1-liter bottle. Next, Product III produced in Example 3 was added to the 1-liter bottle at 1,800 ppm by volume of the hydrocarbon mixture. After stirring for 30 minutes at room temperature, the $H_2S$ level in the head space was reduced to <0.5 ppm.

Turning to Example 6, where 2,150 ppm by volume of sulfide scavenger was required, Example 7 demonstrates a 16% improvement in $H_2S$ scavenging efficiency compared to Product II produced in Example 2. Product III was a more efficient scavenger even though it comprised slightly more inerts than Product II.

While typical embodiments have been set forth for the purpose of illustration, the foregoing descriptions should not be deemed to be a limitation on the scope herein. Accordingly, various modifications, adaptations and alternatives may occur to one skilled in the art without departing from the spirit and scope herein.

What is claimed is:

1. A sulfide scavenger prepared by a method comprising reacting at least one secondary amine with at least one aldehyde and solvent in the presence of a catalyst to form a reaction composition, wherein a reaction temperature is less than or equal to about 90° C. and wherein said catalyst comprises an alkali hydroxide base, said sulfide scavenger comprising an inerts member present therein, said inerts member comprising at least one member selected from the group consisting of diethylmethylamine, dipropylmethylamine (DPMA), dibutylmethylamine (DBMA), N-methyl piperazine, N-methyl piperidine, N-methyl morpholine, and N-N dimethylmethanamine, said inerts member being present in an amount of less than 5 wt %.

2. The sulfide scavenger of claim 1, wherein said base comprises at least one member selected from the group consisting of sodium hydroxide (NaOH) and potassium hydroxide (KOH).

3. The sulfide scavenger of claim 1, wherein a molar ratio of said aldehyde to said secondary amine ranges from about 1.1:1.0 to about 3.0:1.0.

4. The sulfide scavenger of claim 1, wherein said secondary amine comprises at least one member selected from the group consisting of di-n-propylamine and di-n-butylamine.

5. The sulfide scavenger of claim 1, wherein said reaction temperature is less than or equal to about 70° C.

6. The sulfide scavenger of claim 1, wherein said reaction temperature is less than or equal to about 60° C.

7. A method for reducing sulfides from a fluid stream, said method comprising contacting said fluid stream with a sulfide scavenger, wherein said sulfide scavenger was prepared by a method comprising reacting at least one secondary amine with at least one aldehyde and solvent in the presence of a catalyst to form a reaction composition, wherein a reaction temperature is less than or equal to about 90° C. and wherein said catalyst comprises an alkali hydroxide base, said sulfide scavenger comprising an inerts member present therein, said inerts member comprising at least one member selected from the group consisting of diethylmethylamine, dipropylmethylamine (DPMA), dibutylmethylamine (DBMA), N-methyl piperazine, N-methyl piperidine, N-methyl morpholine, and N,N-dimethylmethanamine, said inerts member being present in an amount of less than 5 wt %.

8. The method of claim 7, wherein said sulfides comprise at least one member selected from the group consisting of organic sulfides, mercaptans, thiols, COS, and $H_2S$.

9. The method of claim 7, wherein said sulfides are $H_2S$.

10. The method of claim 7, wherein said fluid stream is a hydrocarbon stream.

11. The method of claim 7, wherein said fluid stream is an aqueous stream.

12. The method of claim 7, wherein said base comprises at least one member selected from the group consisting of sodium hydroxide (NaOH) and potassium hydroxide (KOH).

13. The method of claim 7, wherein said solvent comprises at least one member selected from the group consisting of water and hydrocarbons.

14. The method of claim 7, wherein a molar ratio of said aldehyde to said secondary amine ranges from about 1.1:1.0 to about 3.0:1.0.

15. The method of claim 7, wherein said reaction temperature is less than or equal to about 70° C.

16. The method of claim 7, wherein said reaction temperature is less than or equal to about 60° C.

17. The method of claim 7, wherein a weight percent (wt %) of said catalyst ranges from about 1 wt % to about 5 wt % of a total weight of said reaction composition.

18. The method of claim 7, wherein a weight percent (wt %) of said solvent ranges from about 5 wt % to about 10 wt % of a total weight of said reaction composition.

19. The method of claim 7, wherein said sulfide scavenger is added to said fluid stream in an amount ranging from about 10 to about 100,000 ppm by volume of said fluid stream.

20. The method of claim 7, wherein said sulfide scavenger is added to said fluid stream in an amount ranging from about 100 to about 50,000 ppm by volume of said fluid stream.

21. The method of claim 7, wherein said sulfide scavenger is added to said fluid stream in an amount ranging from about 600 to about 3,000 ppm by volume of said fluid stream.

* * * * *